United States Patent
Solitro et al.

(10) Patent No.: US 11,116,490 B2
(45) Date of Patent: Sep. 14, 2021

(54) EXPANDABLE SOFT TISSUE PROTECTOR

(71) Applicant: Board of Supervisors of Louisiana State University and Agricultural and Mechanical College, Baton Rouge, LA (US)

(72) Inventors: Giovanni Francesco Solitro, Shreveport, LA (US); Massimo Morandi, Bloomfield Hills, MI (US); R. Shane Barton, Shreveport, LA (US)

(73) Assignee: Brd. of Sup. of LSU and A &MColleg, Baton Rouge, LA (US)

(*) Notice: Subject to any disclaimer, the term of this patent is extended or adjusted under 35 U.S.C. 154(b) by 102 days.

(21) Appl. No.: 16/798,666

(22) Filed: Feb. 24, 2020

(65) Prior Publication Data

US 2020/0330087 A1 Oct. 22, 2020

Related U.S. Application Data

(60) Provisional application No. 62/809,180, filed on Feb. 22, 2019.

(51) Int. Cl.
*A61B 1/32* (2006.01)
*A61B 17/02* (2006.01)
*A61B 90/00* (2016.01)

(52) U.S. Cl.
CPC ...... *A61B 17/0293* (2013.01); *A61B 17/0218* (2013.01); *A61B 90/39* (2016.02); *A61B 2017/0275* (2013.01); *A61B 2090/3966* (2016.02)

(58) Field of Classification Search
USPC .......................................... 600/208
See application file for complete search history.

(56) References Cited

U.S. PATENT DOCUMENTS

| 8,177,785 | B2 | 5/2012 | Vaidya |
| 2004/0082969 | A1* | 4/2004 | Kerr ................. A61B 17/0206 606/205 |

OTHER PUBLICATIONS

Rahul Vaidya et al., www.jorthotrauma.com, "Treatment of Unstable Pelvic Ring Injuries With an Internal Anterior Fixator and Posterior Fixation: Initial Clinical Series", J Orthop Trauma, vol. 26, No. 1, Jan. 2012, pp. 1-8.
Daniel Hesse et al., www.jorthotrauma.com, "Femoral Nerve Palsy After Pelvic Fracture Treated With INFIX: A Case Series", J Orthop Trauma, vol. 29, No. 3, Mar. 2015, pp. 138-143.
M. Kuttner et al., "Der subkutane ventrale Fixateur interne (SVFI) am Becken", Unfallchirurg 2009—112:661-669 DOI 10.1007/s00113-009-1623-0.
T. Apivatthakakul et al., http://dx.doi.org/10.1016/j.injury.2016.08.006, "Anterior subcutaneous pelvic internal fixator (INFIX), Is it safe?" A cadaveric study, Injury, Int. J. Care Injured 47 (2016) 2077-2080.

(Continued)

*Primary Examiner* — Sameh R Boles
(74) *Attorney, Agent, or Firm* — Holoubek Patent Law, L.L.C.; Charlotte Holoubek

(57) ABSTRACT

A soft tissue protector comprising a hollow body, a plurality of jaws at an anterior end of the hollow body forming a conical tip, an insert that is inserted inside of a posterior end of the hollow body, at least one handle, and a sliding lock on the handle that retains the insert inside of the hollow body.

19 Claims, 16 Drawing Sheets

(56) References Cited

OTHER PUBLICATIONS

Christian Fang et al., "Complications after percutaneous internal fixator for anterior pelvic ring injuries", International Orthopaedics (SICOT) (2017) 41:1785-1790.

Massimo Morandi et al., wileyonlinelibrary.com, "Safe Supra-Acetabular Pin Insertion in Relation to Intraosseous Depth", Journal of Orthopaedic Research® Aug. 2019, DOI 10.1002/jor.24323, pp. 1790-1797.

* cited by examiner

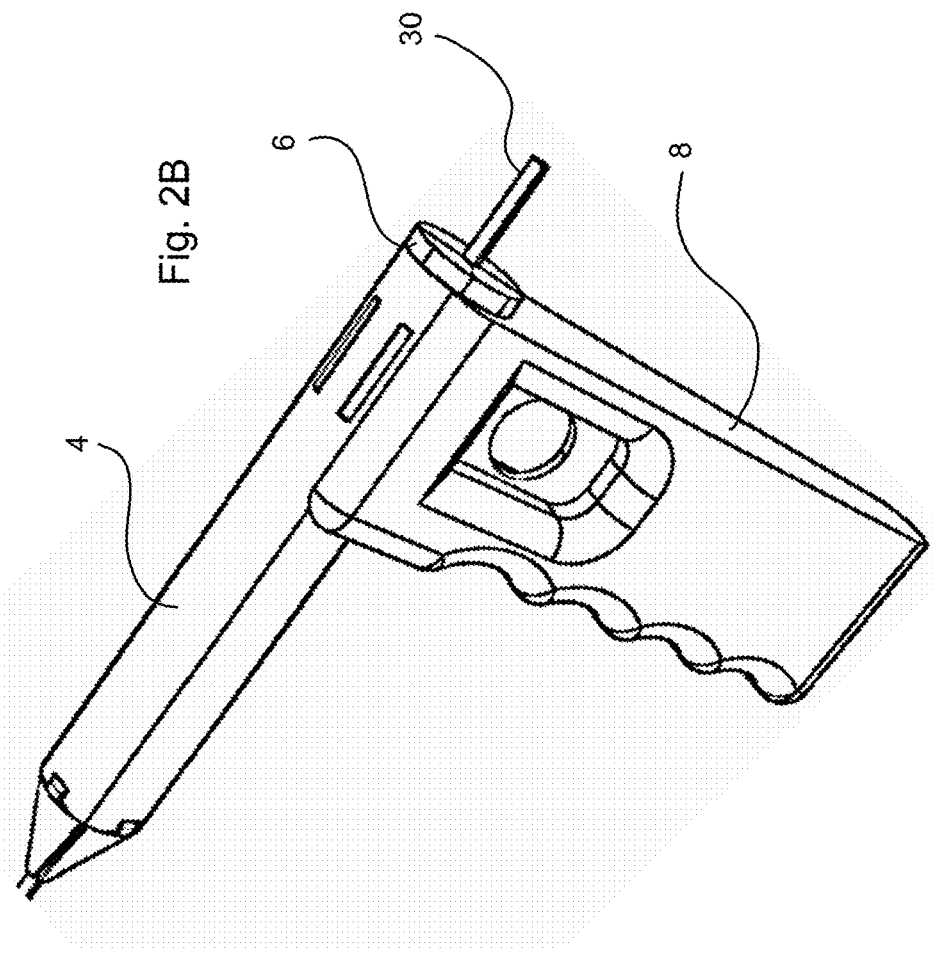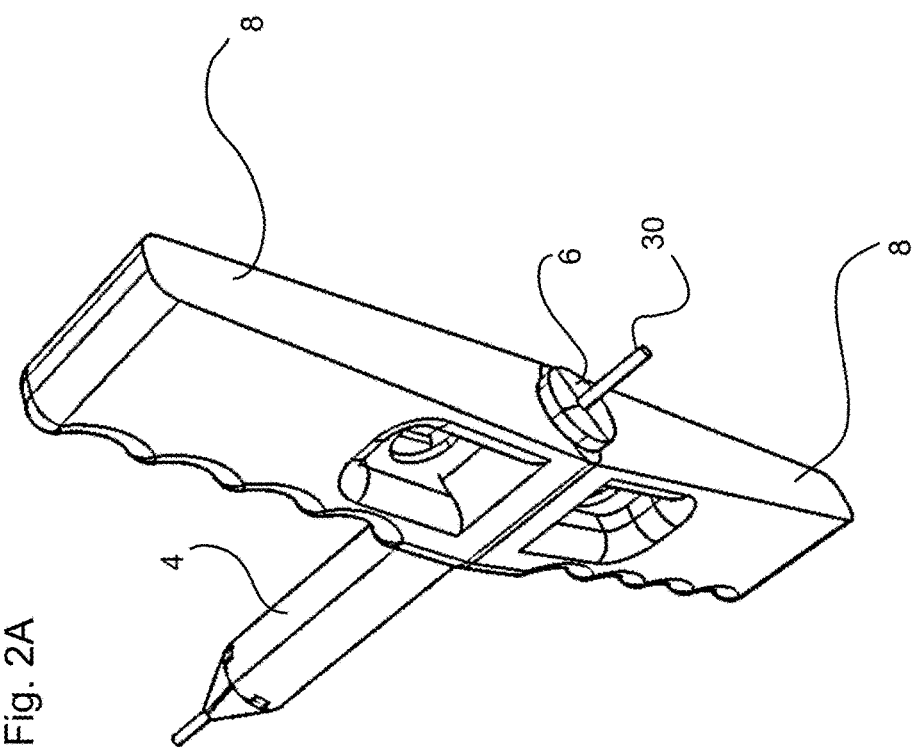

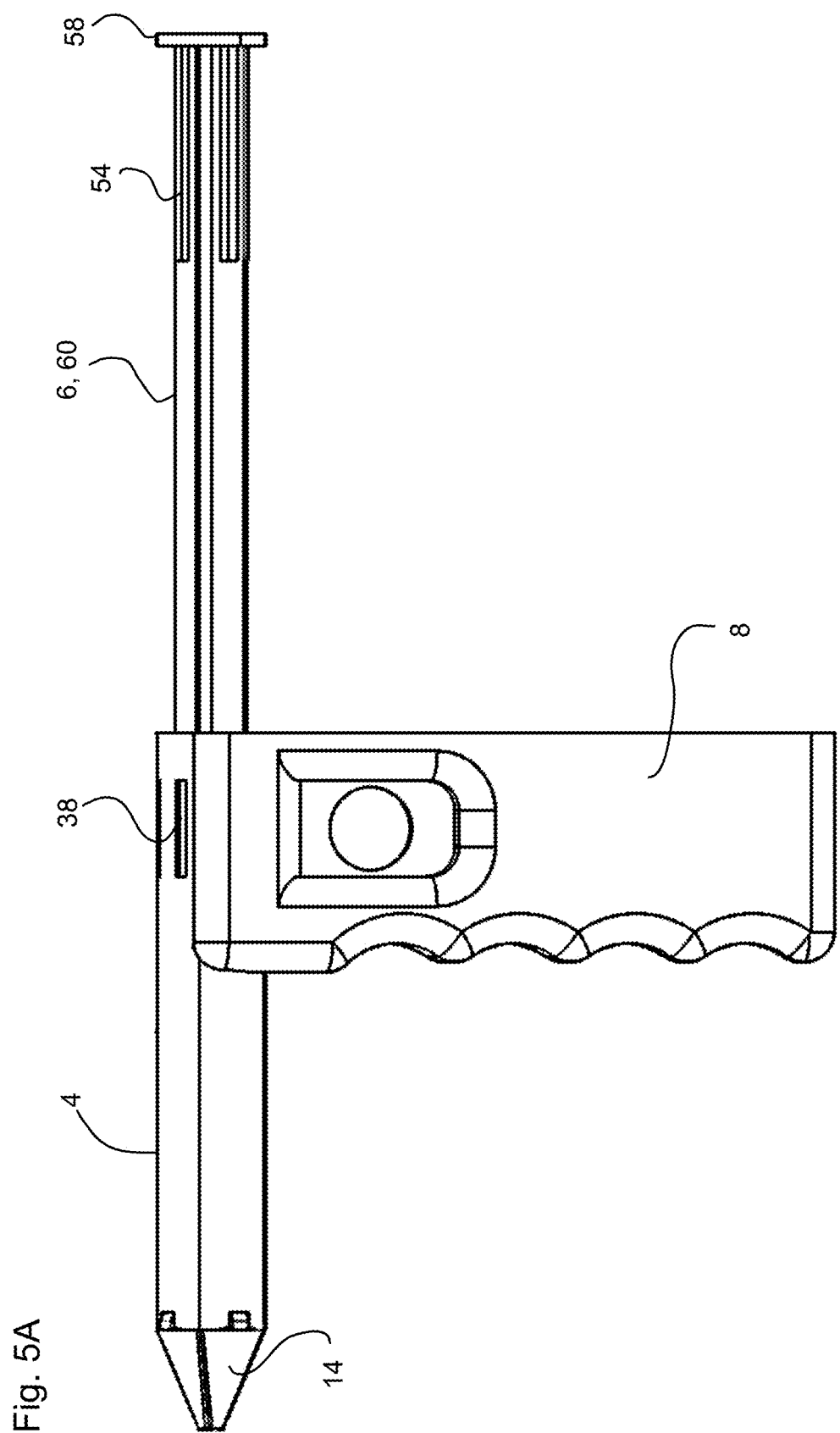

Fig. 8B
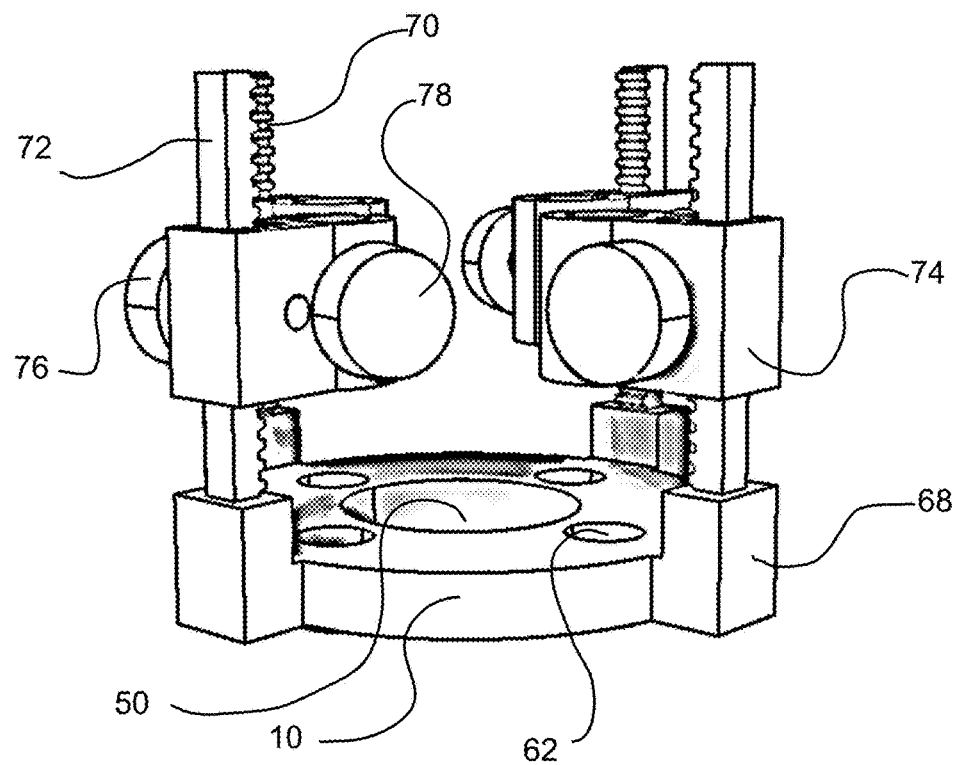
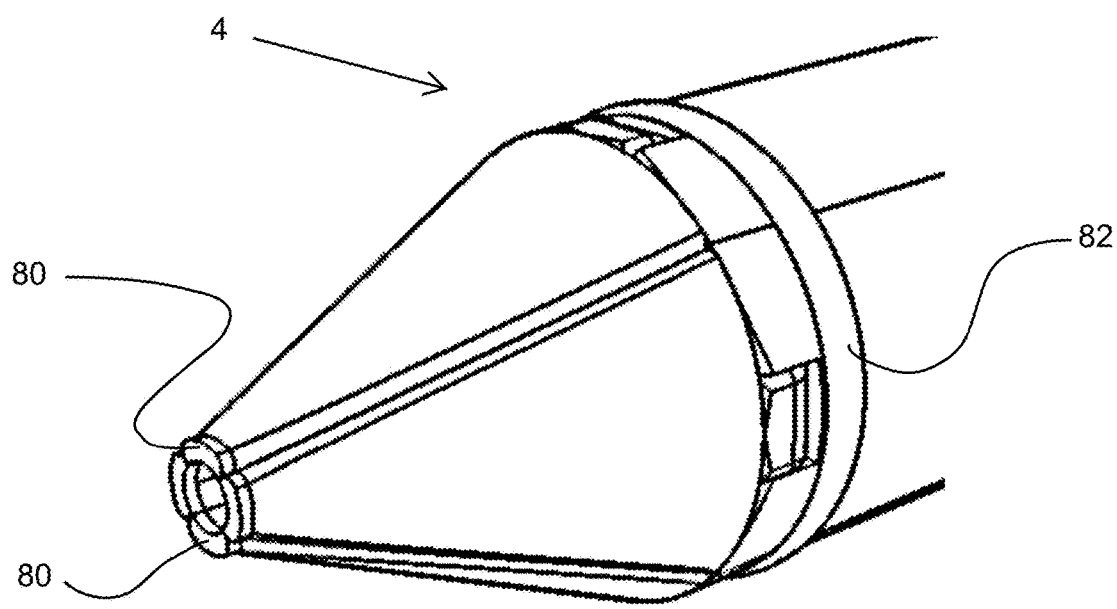
Fig. 9

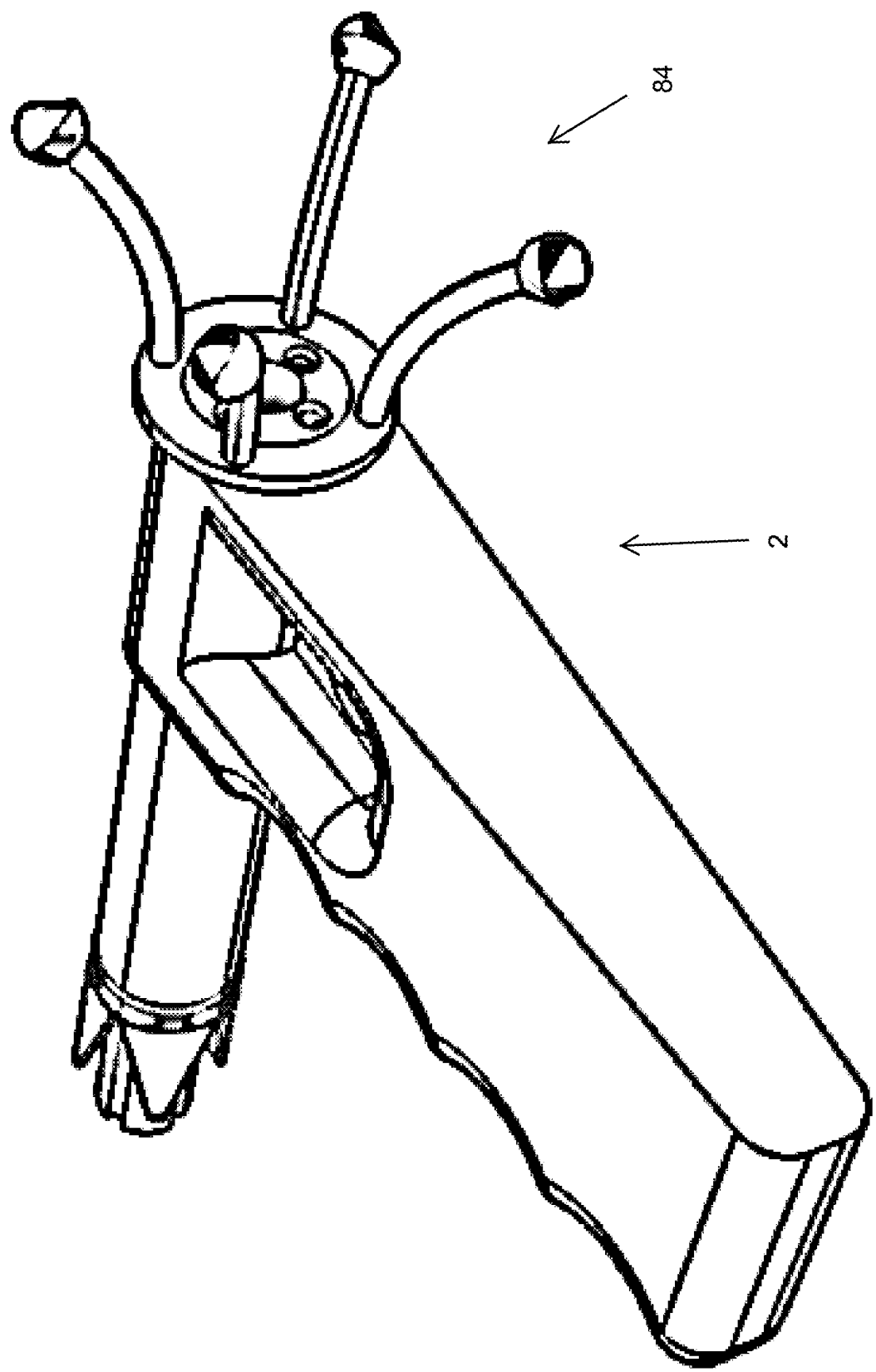

EXPANDABLE SOFT TISSUE PROTECTOR

CROSS REFERENCE TO RELATED APPLICATIONS/PRIORITY

The present invention claims priority to U.S. Provisional Patent Application No. 62/809,180 filed Feb. 22, 2019, which is incorporated by reference into the present disclosure as if fully restated herein. Any conflict between the incorporated material and the specific teachings of this disclosure shall be resolved in favor of the latter. Likewise, any conflict between an art-understood definition of a word or phrase and a definition of the word or phrase as specifically taught in this disclosure shall be resolved in favor of the latter.

BACKGROUND

With recent developments, several surgical procedures are performed through small incisions. These surgical approaches have several advantages such as reduced pain, fewer complications, and reduced hospital stay. However, in certain anatomical structures, and especially for obese patients, the access of instrument can be challenging and can results in damage of surrounding structures such as nerves or ligaments.

A surgical procedure that can be harmful using current technology, just as an example, is the subcutaneous anterior internal fixation. It is used for rotationally and vertically unstable pelvic injuries and is performed through two three-cm incision performed bilaterally at the anterior inferior iliac spine. This technique can result in femoral nerve palsy and lateral femoral cutaneous nerve (LFCN) inflammation. These structures are the closest anatomical elements to the hardware and inflammation of the LFCN can be limited at time of surgery limiting the impingement of the nerve through proper tools insertion, though such insertion is challenging for surgeons. Existing soft tissue protectors are generally composed by a cylinder of constant diameter that hosts a conical insert. After removal of the conical insert the cylindrical portion is pressed against the bone with consequent soft tissue impingement or it is kept in place with exposure of the tools to soft tissues contact causing damage. For the foregoing reasons, there is a pressing, but seemingly irresolvable need for a soft tissue protector for surgery.

SUMMARY

Wherefore, it is an object of some embodiments of the present invention to overcome the above-mentioned shortcomings and drawbacks associated with the current technology.

The presently disclosed invention relates to methods of using and soft tissue protectors comprising a hollow body, a plurality of jaws at an anterior end of the hollow body forming a conical tip, and an insert that is inserted inside of a posterior end of the hollow body. According to further embodiments, the soft tissue protector includes at least one handle. According to further embodiments, the soft tissue protector includes a sliding lock on the handle that retains the insert inside of the hollow body. According to further embodiments, the soft tissue protector includes two handles, mounted on opposite radial sides of the hollow body. According to further embodiments, the insert has one or more radial tabs extending axially along a radially exterior surface, the radial tabs aligning with tab grooves axially extending along a radially inner surface of an interior of the hollow body. According to further embodiments, the plurality of jaws is spring biased in a closed position. According to further embodiments, an anterior end of the plurality of jaws define a central hole that allows passage to one of a surgical pin or a Kirschner wire. According to further embodiments, a post hole is defined along an inner surface of each of the jaws, and a corresponding post is placed at an anterior end of the insert, each post being aligned with a respective post hole and locking each respective jaw in a closed position. According to further embodiments, a central pathway is defined by an inner radial surface of the insert, allowing the passage of surgical tools within. According to further embodiments, one or more pockets are present in a radially exterior surface of the insert and a radially interior surface of the hollow body, the pockets sized to support and allow passage of one of a surgical pin or a Kirschner wire. According to further embodiments, the soft tissue protector includes a clamp, which axially secures the one of a surgical pin or a Kirschner wire in a stationary axial position relative to the soft tissue protector. According to further embodiments, the clamp includes a rack and pinon. According to further embodiments, there are four pocket and a rack and pinon unit for each pocket. According to further embodiments, the soft tissue protector includes a radiopaque insert on the hollow body. According to further embodiments, the radiopaque insert is a radiopaque tip insert and is disposed on anterior end of one or more jaws. According to further embodiments, the radiopaque insert is a radiopaque ring insert and is disposed around an outer circumference of the hollow body, adjacent to the anterior end of the hollow body. According to further embodiments, the soft tissue protector includes a navigation marker attached to a posterior end of the hollow body. According to further embodiments, the navigation marker is an inertial marker. According to further embodiments, the soft tissue protector includes an optical marker.

The presently disclosed invention if further related to methods of use and soft tissue protectors comprising, a hollow body, a plurality of jaws at an anterior end of the hollow body forming a conical tip, the plurality of jaws is spring biased in a closed position, an insert that is inserted inside of a posterior end of the hollow body, at least one handle, a sliding lock on the handle that retains the insert inside of the hollow body, tab grooves axially extending along a radially inner surface of an interior of the hollow body, a plurality of radial tabs extending axially along a radially exterior surface of the insert, the radial tabs aligning with tab grooves, a central hole defined in an anterior end of the plurality of jaws, the central hole allowing passage of one of a surgical pin or a Kirschner wire, a post hole being defined along an inner surface of each of the jaws, a post is placed at an anterior end of the insert, each post being aligned with a respective post hole and locking each respective jaw in a closed position when the insert is sufficiently inserted into the hollow body, a central pathway is defined by an inner radial surface of the insert, allowing the passage of surgical tools within, four pockets are present in a radially exterior surface of the insert and a radially interior surface of the hollow body, the pockets sized to support and allow passage of one of a surgical pin or a Kirschner wire, a clamp, which axially secures the one of a surgical pin or a Kirschner wire in a stationary axial position relative to the soft tissue protector; the clamp including a rack and pinon unit for each pocket, and one of a radiopaque tip insert disposed on anterior end of one or more jaws, a radiopaque ring insert disposed around an outer circumference of the hollow body, adjacent to the anterior end of the hollow body, an optical navigation marker attached to a posterior end of the hollow body, and an inertial navigation marker attached to a posterior end of the hollow body.

The invention consists of a tool that can be used at time of surgery during hardware insertion, typically bone screws, to protect surrounding structures.

The presently claimed invention relates to drilling guides and soft tissue protectors used for minimally invasive surgeries, including for the placement of bone screws and Kirschner wires.

The presently claimed invention is related to a tool with an expandable conical tip that enlarges the patient surgical cavity minimizing risk of impingement and tool exposure to soft tissues. The invention can be anchored to the bone to preserve the position of the created cavity and also allows fine adjustment of its orientation in relation to the connected bone.

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which:

FIGS. 2A and 2B are back top perspective views of the tissue protector in FIG. 1A, with the tissue protector in 2A having a second handle attached to the hollow body;

FIG. 5A is a side isometric view of the tissue protector of FIG. 1B, with the jaws closed and a cylindrical insert being partially inserted inside of the hollow body;

FIG. 8B is side perspective view of the clamp shown in FIG. 8

FIG. 9 is an up-close partial perspective view of the anterior end of the tissue protector of FIG. 3A;

FIG. 11 is a rear bottom side perspective view of tissue protector and insert of FIG. 5B, with optical markers attached at the posterior end of the hollow body.

DETAILED DESCRIPTION

Figure 1A:
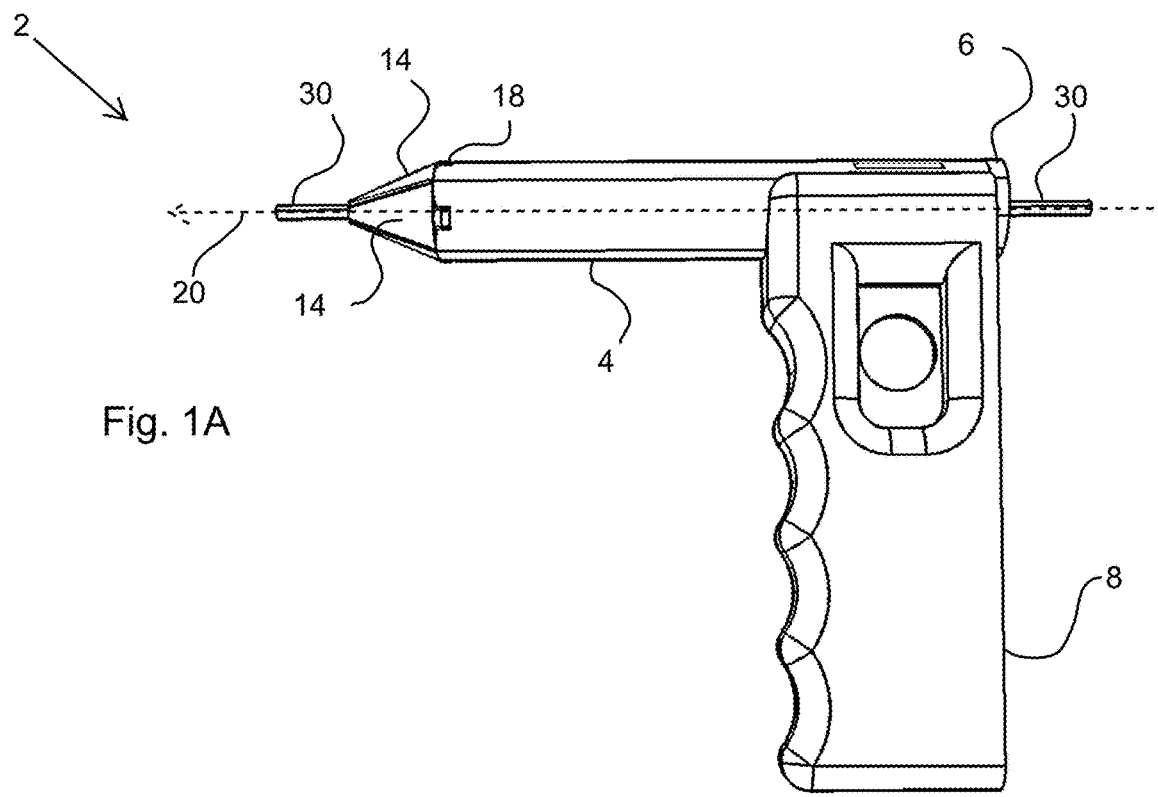
FIGS. 1A and 1B are side isometric views of the tissue protector in a closed position with a locking insert and K wire (FIG. 1A) and empty in the open position (FIG. 1B).

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40% means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

Turning now to FIG. 1A to FIG. 11, a brief description concerning the various components of the present invention will now be briefly discussed. As can be seen in this embodiment, the invention relates to soft tissue protectors 2 and methods of using the soft tissue protectors. The soft tissue protectors comprise a hollow body 4 and an insert 6. The soft tissue protector may optionally include one or more handles 8, a clamp 10, and a marker 12, as described further below.

The hollow body 4 includes a plurality of radially disposed jaws 14, located on an anterior end 16 of the hollow body 4. The jaws 14 are convergent to a point when closed. The jaws 14 are preferably spring biased at respective hinges 18 in the closed position, such that they may be opened by applying force in the anterior direction 20 on an inner wall of the jaws 22, but that they will remain closed without such force, or will reclose when such force is removed. Optionally, the jaws 14 may just be manually pivotable on the anterior end 16 of the hallow body 4, and not spring biased, to minimize complexity and chance of malfunction of the soft tissue protector 2.

On an inner surface 22 of each jaw 4 is preferably a non-through post hole 24, which extends concavely into the inner surface 22 of the jaw. When the jaws 14 are open, they allow the full inner width of the hollow body interior 26 to be accessible. When the jaws are closed, there preferably remains a small central hole 28, sized to fit a surgical pin or Kirschner wire 30 (K-wire), used for guidance, for example. The central hole 28 being defined by the anterior ends 32 of each of the jaws 14. The insert 6 is inserted into the hollow body interior 26 in the posterior end 34 of the hollow body 4.

Figure 1B:
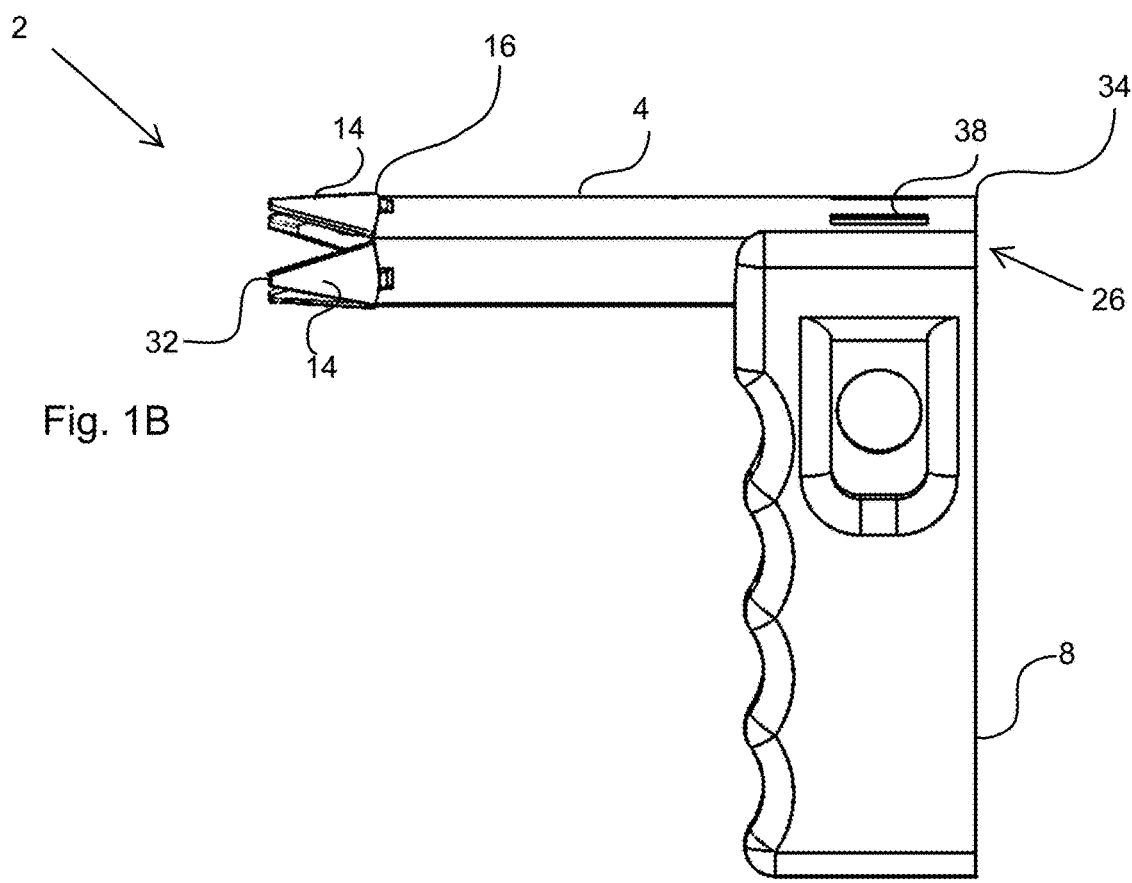

Preferably, during the soft tissue protector's 2 insertion, the jaws 14 will be in the closed position, as shown in FIG. 1A. After insertion, the jaws 14 could be opened to expand the hosting tissues, as shown in FIG. 1B. The soft tissue protector 2 preferably is equipped with a removable handle 8.

The soft tissue protector 2 is an expandable conical tissue protector that enlarges the cavity minimizing risk of impingement and tool exposure to soft tissues during surgery. The soft tissue protector 2 can be anchored to the bone of the patient to preserve the position of the created cavity and allows fine orientation adjustments.

Figure 2D:
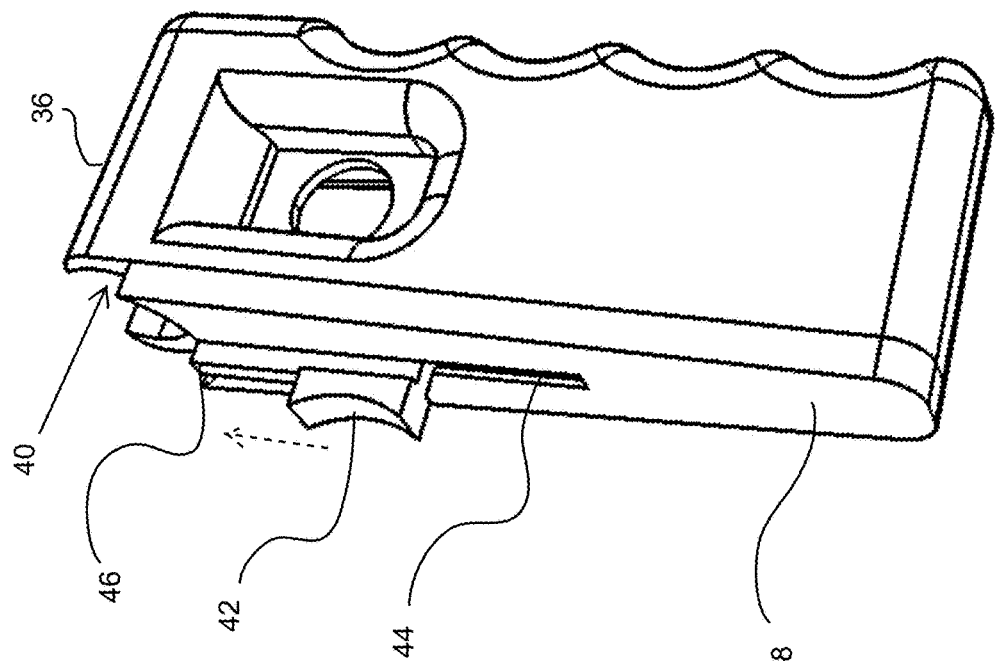
FIGS. 2C and 2D are perspective views of the hollow body and the handle of the tissue protector of FIG. 1A.
Figure 2C:
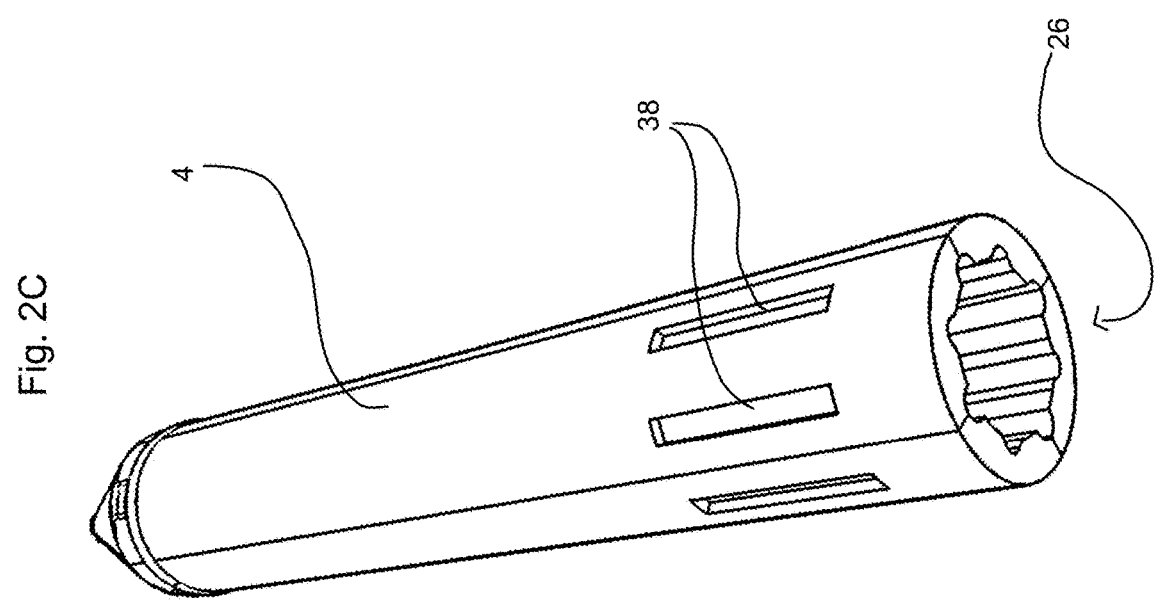

The handle 8 can be used to manipulate the soft tissue protector 2 with two hands (FIG. 2A), one hand (FIG. 2B), or the handle 8 can also be removed from the hollow body 4 to avoid interference with other tools or tissues (FIG. 2C). The handle 8 snaps into the hollow body 4 with a pair of clasps 36 on the handle 8 that engage a pair of recesses 38 on the hollow body 4, releasably retaining the hollow body within a channel 40 on the handle. Additionally, the handle 8 may have a sliding lock 42, that retains the inserts 6 within the hollow body 4. The sliding lock 42 can be easily thumb actuated, sliding from a lower disengaged position along a recessed lock slide 44 in the posterior side of the handle 8, to an upper engaged position, forcing a barrier 46 to a position behind a posterior portion of the insert 6, and thus retaining the insert 6 inside of the hollow body 4. Alternatively, the recesses 38 can be in the form of slots, and the lock barrier 46 can slide into one or more of the recesses 38 when moved into the locking position, and provide locking presser on the insert 6.

Figure 3A:
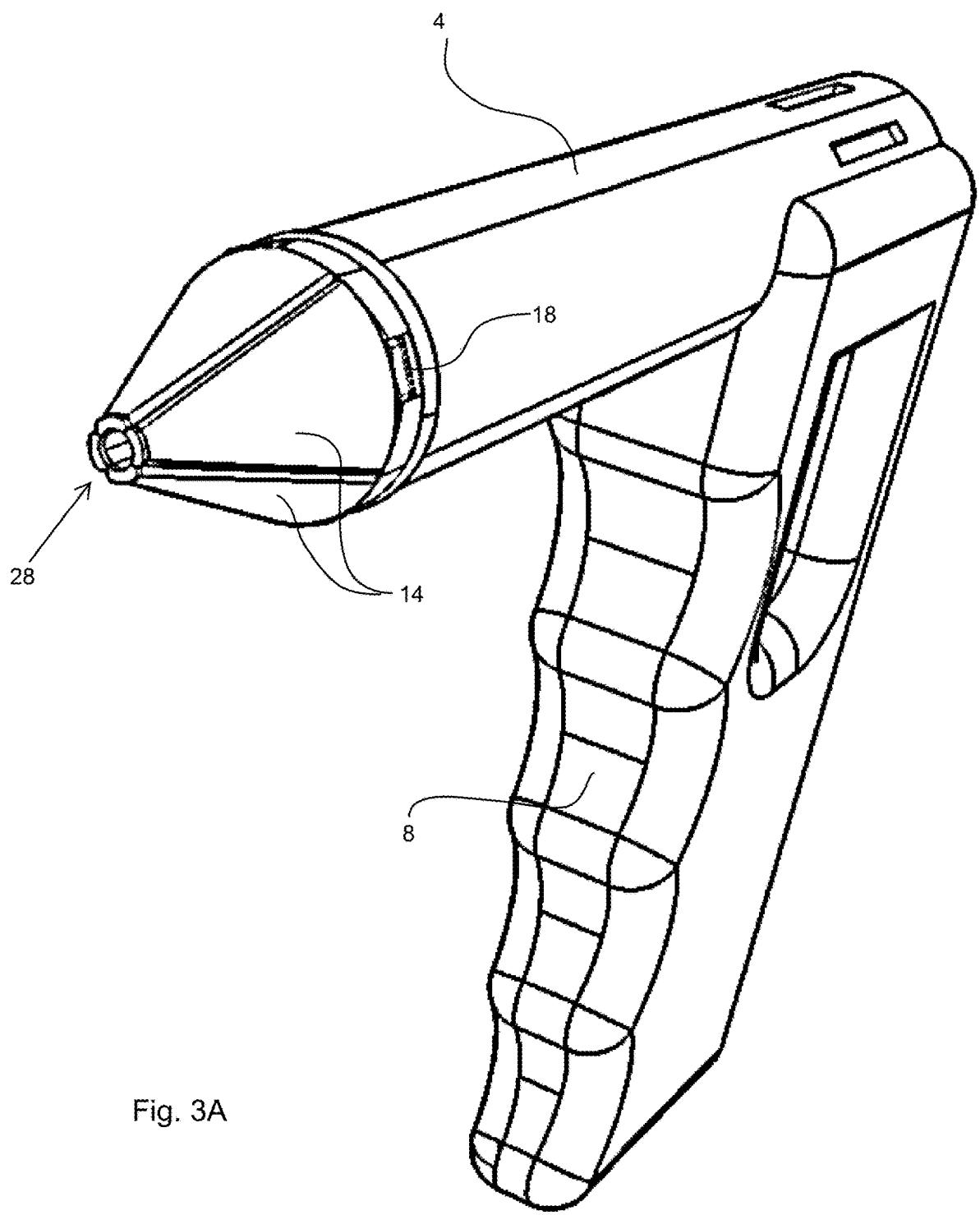
FIG. 3A is a top, front, side perspective view of the tissue protector of FIG. 1B, but with the jaws in the closed position.
Figure 3B:
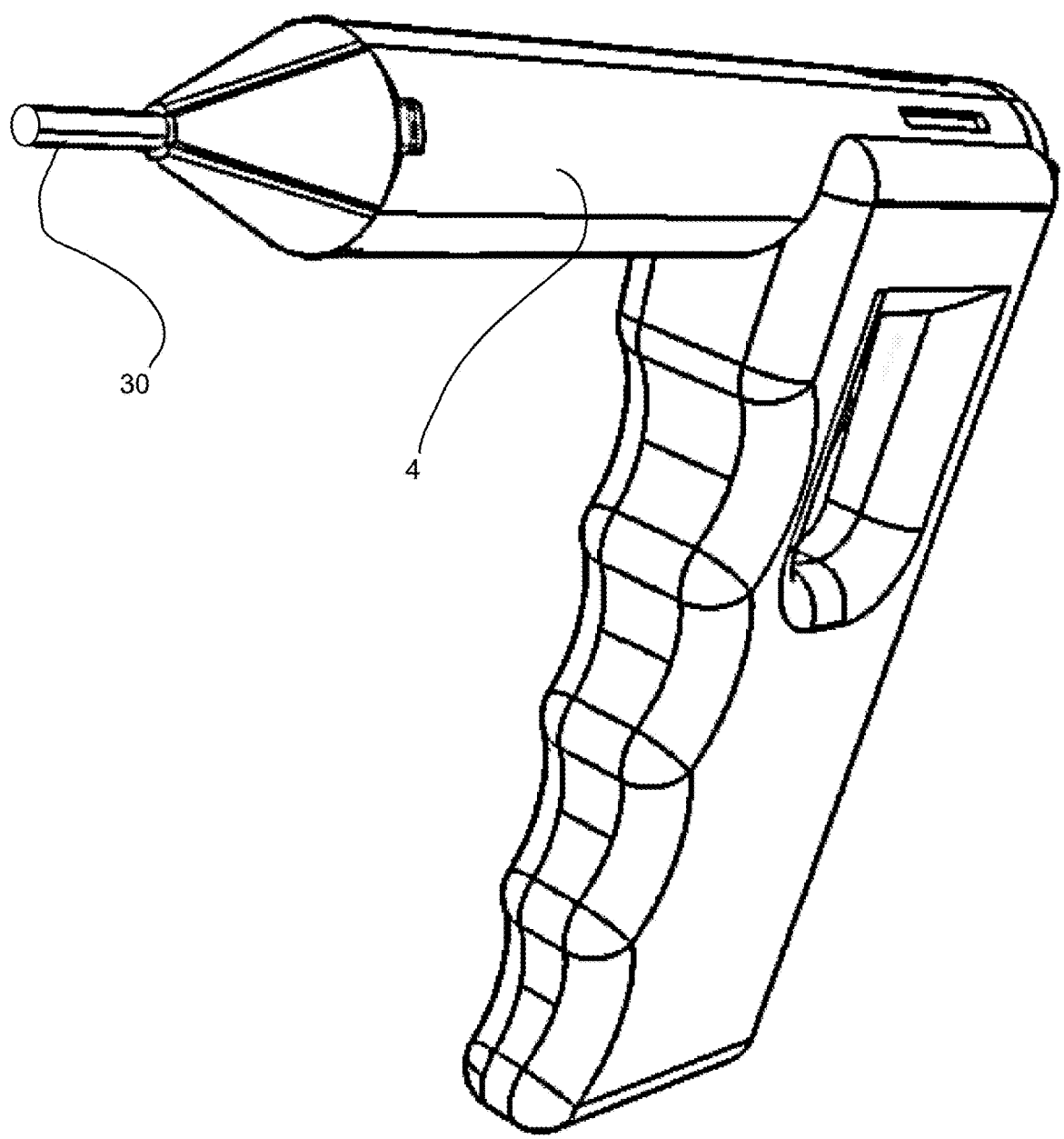
FIG. 3B is a top, front, side perspective view of the tissue protector of FIG. 1A.
Figure 3C:
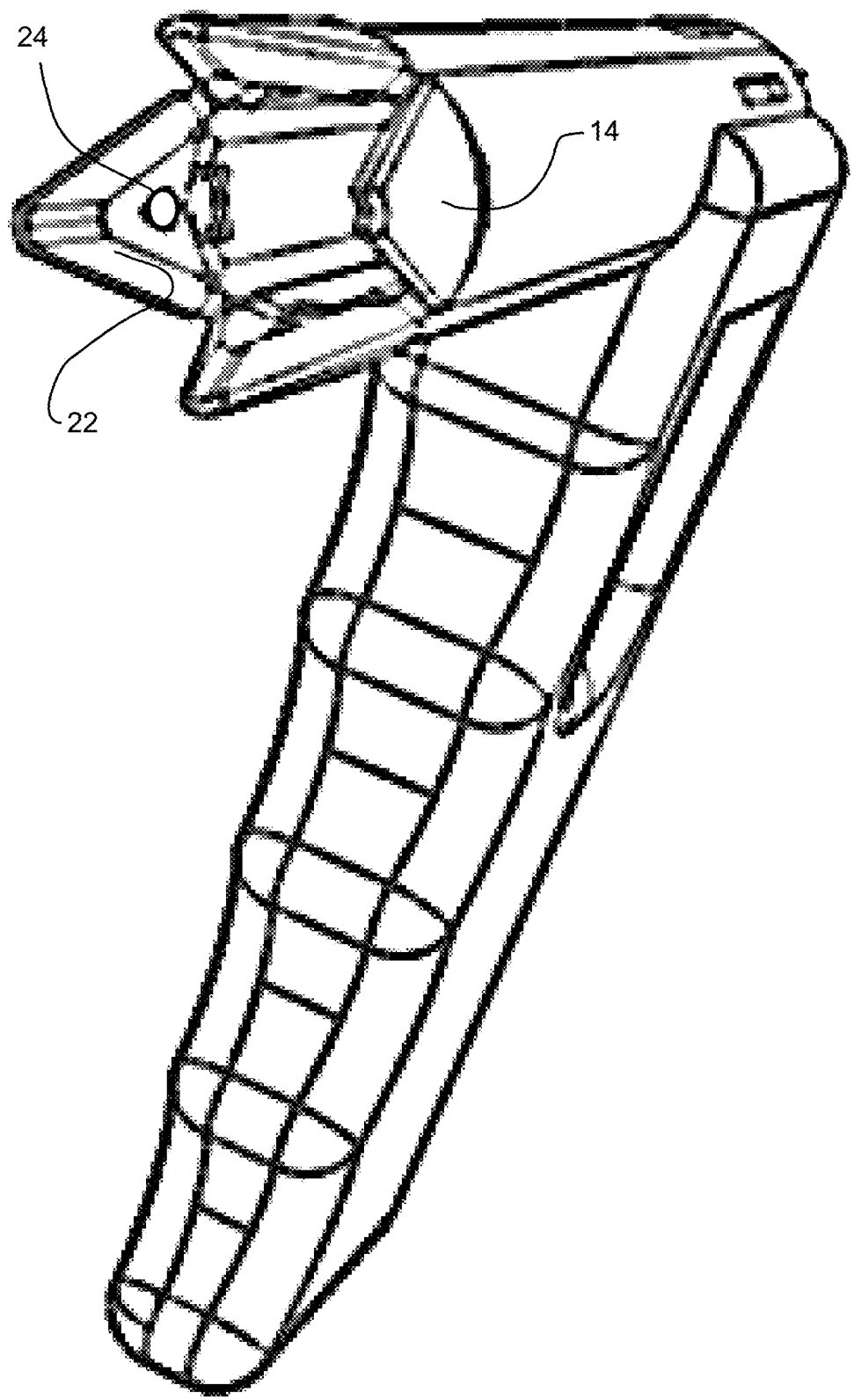
FIG. 3C is a top, front, side perspective view of the tissue protector of FIG. 1A

Turning to FIGS. 3A to 3C, the soft tissue protector 2 is shown in an unexpanded position while not hosting a K-wire 30, hosting a K-wire 30, and the soft tissue protector 2 with the jaws 14 expanded.

Figure 4A:
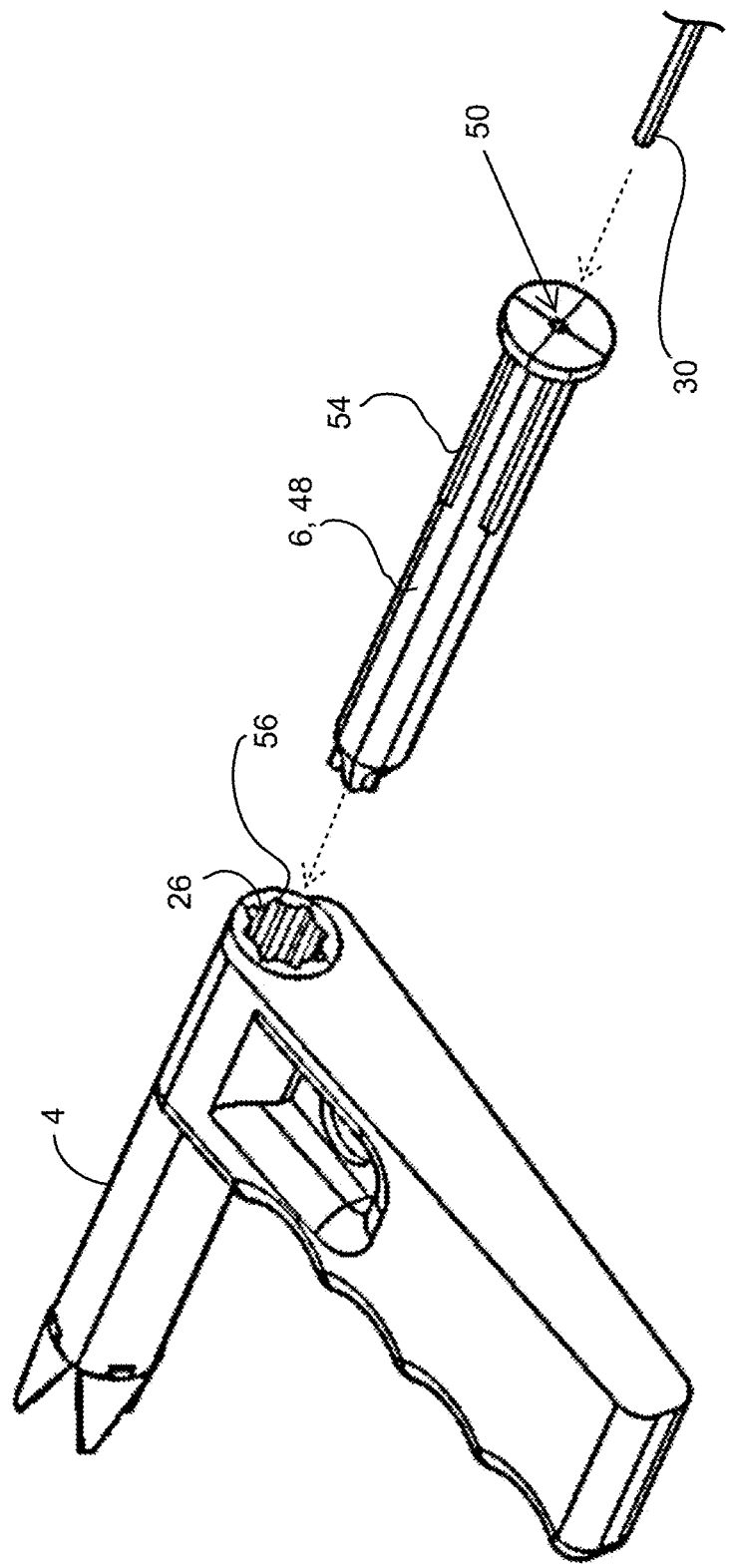
FIG. 4A is an exploded view of the tissue protector of FIG. 1A, but with the jaws in an open position.
Figure 4B:
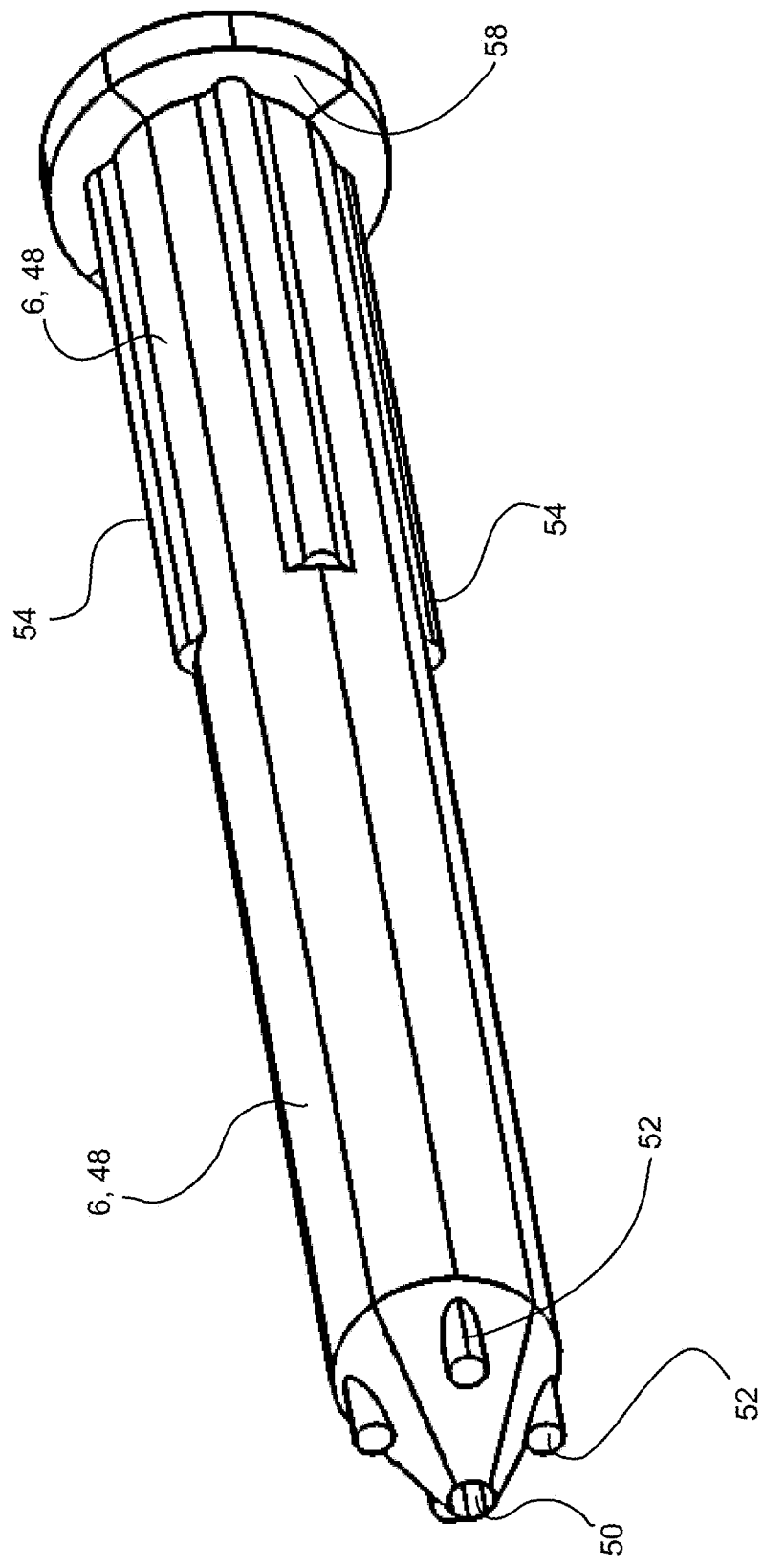
FIG. 4B is a front side top perspective view of the locking insert of FIG. 4A.

Turning to FIGS. 4A and 4B, the hollow body 2 can also host an insert 6 inside the hollow body interior 26. The insert shown in FIGS. 4A and 4B is a locking insert 48. It is hollow, to allow the insertion of a K-wire into a central pathway 50 and stabilizes the directionality of the central K-wire 30 in place. The locking insert 48 has posts 52 on an anterior end that fit within the post holes 24 in the jaws 4 and keep the hollow body 4 in closed position. An anterior end of the posts 52 sit completely inside the post holes 24 of the jaws 14 when the locking insert 48 is inserted fully into the hollow body 4.

The inserts 6 may also be provided with radial tabs 54 that extend axially along an outer surface of the inserts 6. These tabs 54 will align and mate with tab grooves 56 extending axially along the inner walls of the hollow body interior 26. This aids in the insertion of the inserts 6 into the hollow body 4, and prevents axial rotation of the insert 6 within the hollow body 4. In some embodiments, the inserts 6 have a base 58 that extends radially at the posterior side of the insert 6, to prevent the insert 6 from being over inserted into the hollow body 4.

Figure 5B:
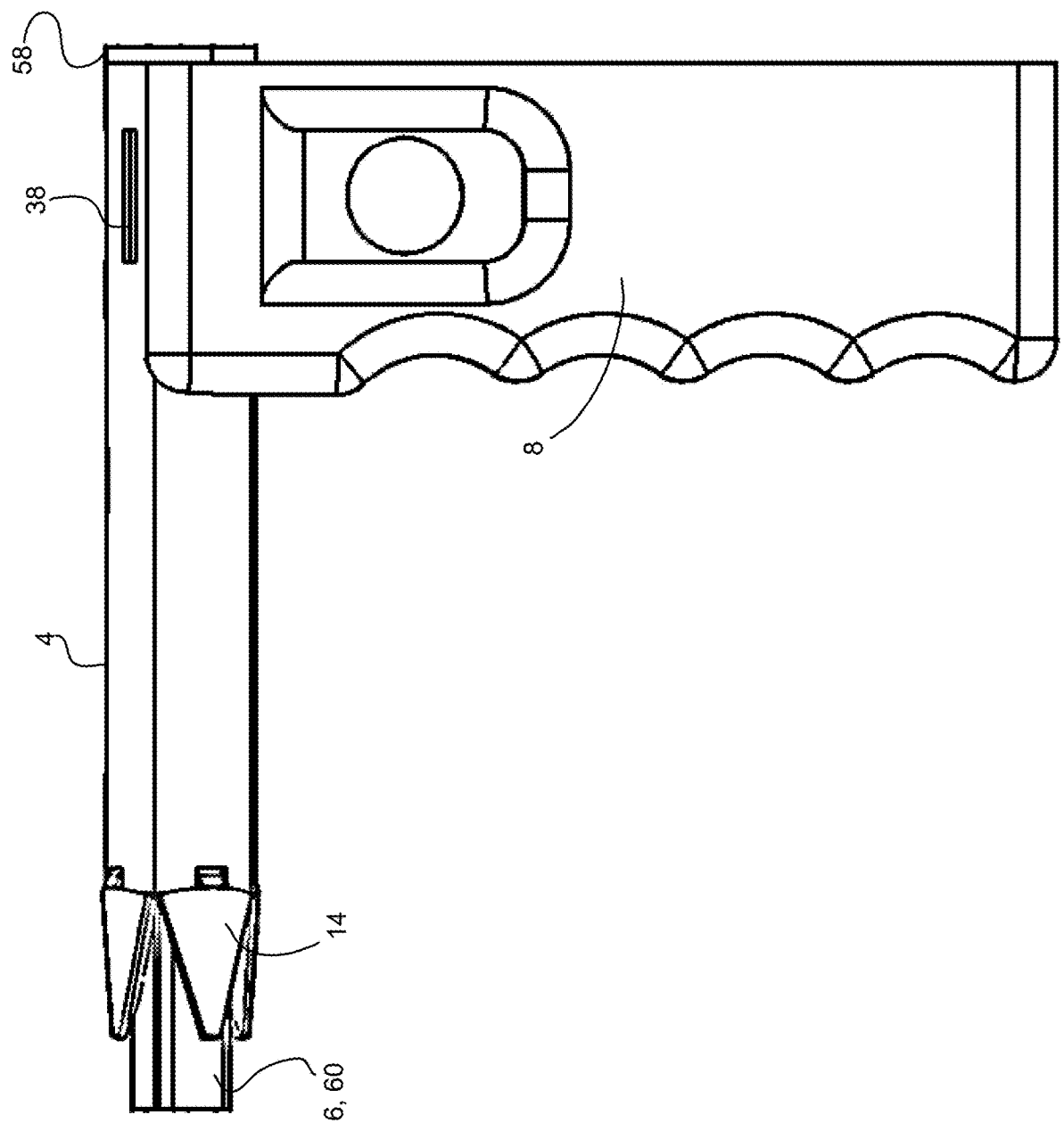
FIG. 5B is a side isometric view of the tissue protector of FIG. 1B, with the cylindrical insert being fully inserted.
Figure 5C:
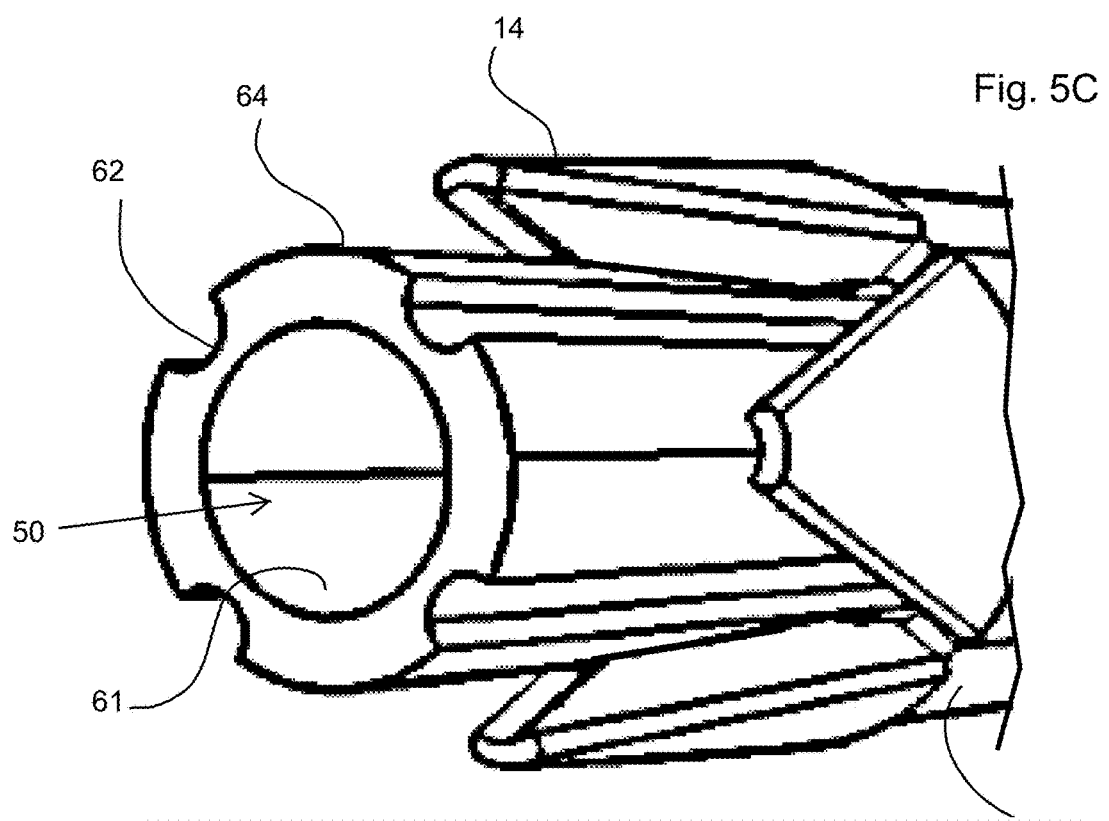
FIG. 5C is a up close partial perspective view of the tissue protector and cylindrical insert of FIG. 5B.

The soft tissue protector 2 opening can be performed by a cylindrical insert 60, as shown in FIGS. 5A to 5C. At the insertion of cylindrical insert 60 the jaws 14 are pushed outward as shown in FIGS. 5B and 5C. The cylindrical insert 60 may also have a central pathway defined by an inner radial surface 61

Figure 6:
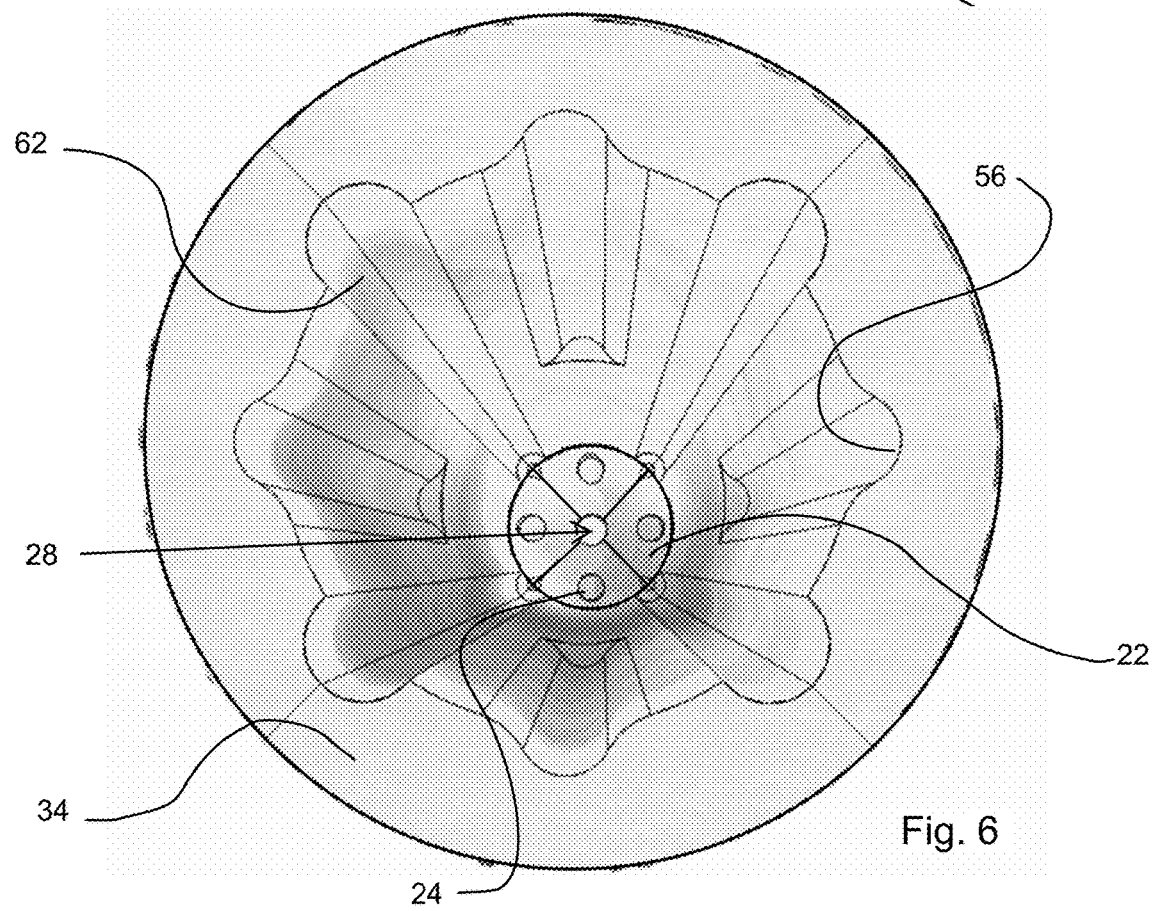
FIG. 6 is a rear perspective view of the inside of the tissue protector of FIG. 1B, but with the jaws in the closed position.
Figure 7B:
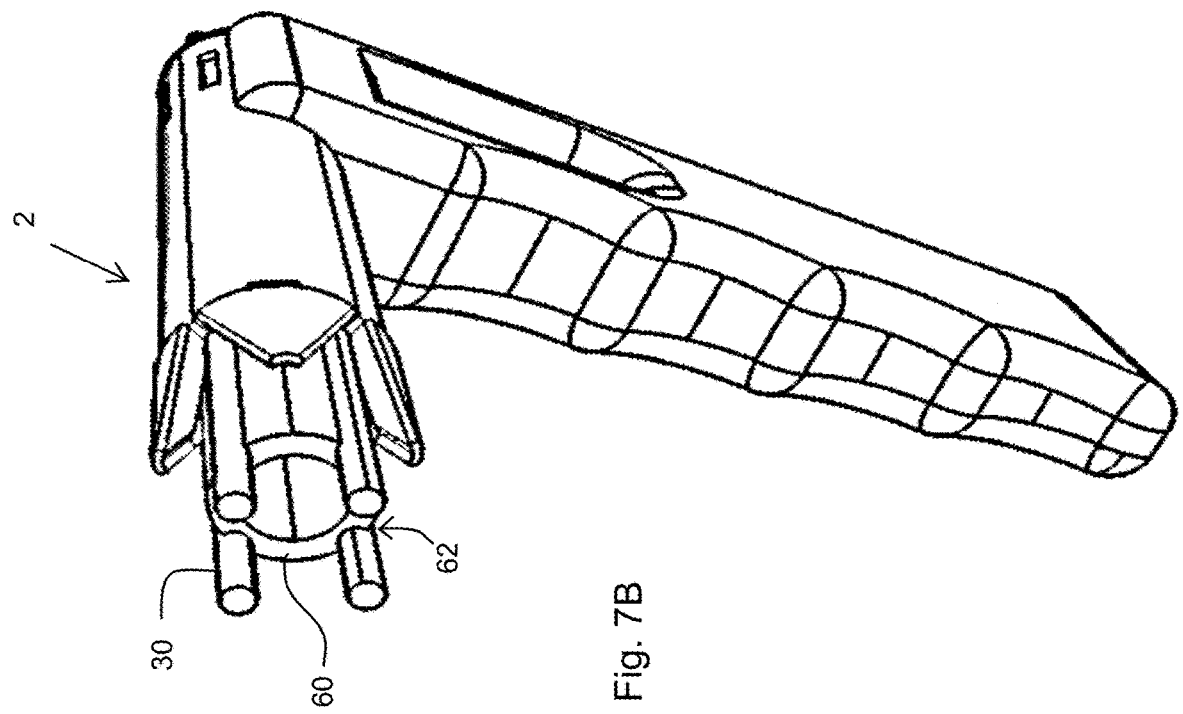
FIGS. 7A and 7B are rear bottom side and front top side perspective views of the tissue protector of FIG. 5B, with the cylindrical insert stabilizing four K wires.
Figure 7A:
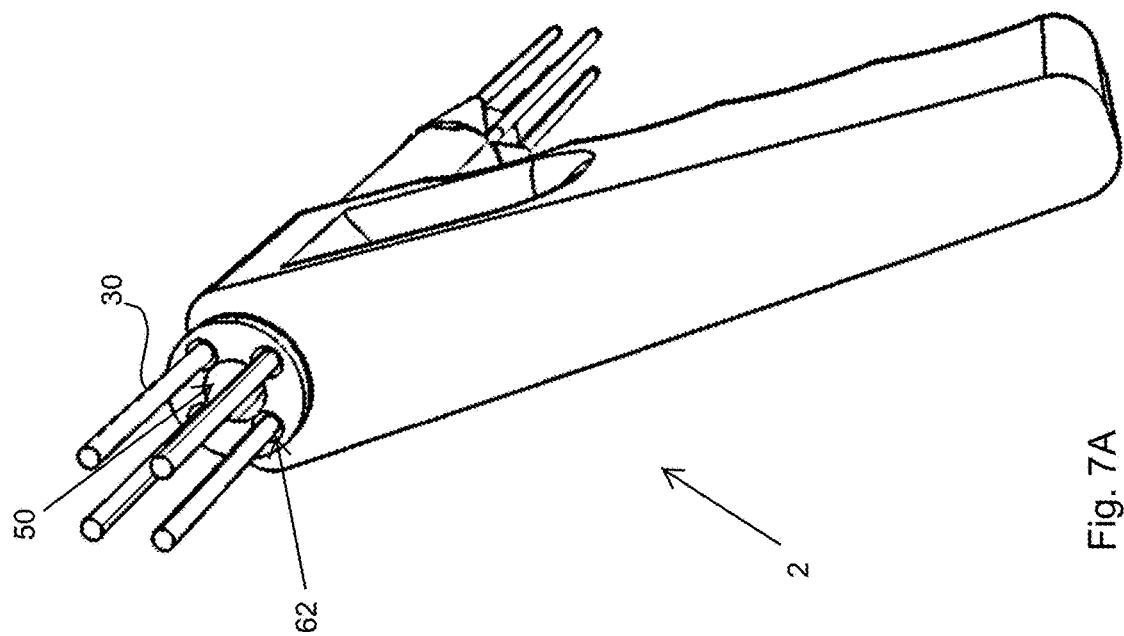

The soft tissue protector 2 tool can have partial or full pockets 62 to host k-wires or pins 30 along the inner perimeter of the hollow body interior 26 and/or the outer perimeter 64 of the insert 6. In FIGS. 6, 7A, and 7B, an embodiment is shown where half pockets 62 are defined in both the inner perimeter of the hollow body interior 26 and the outer perimeter 64 of the insert 6. With the posterior view of the hollow body 4, shown in FIG. 6, the tab grooves 56 for the radial tabs 54 and the pockets 62 for the partially contained k-wires 30 are shown.

Figure 8A:
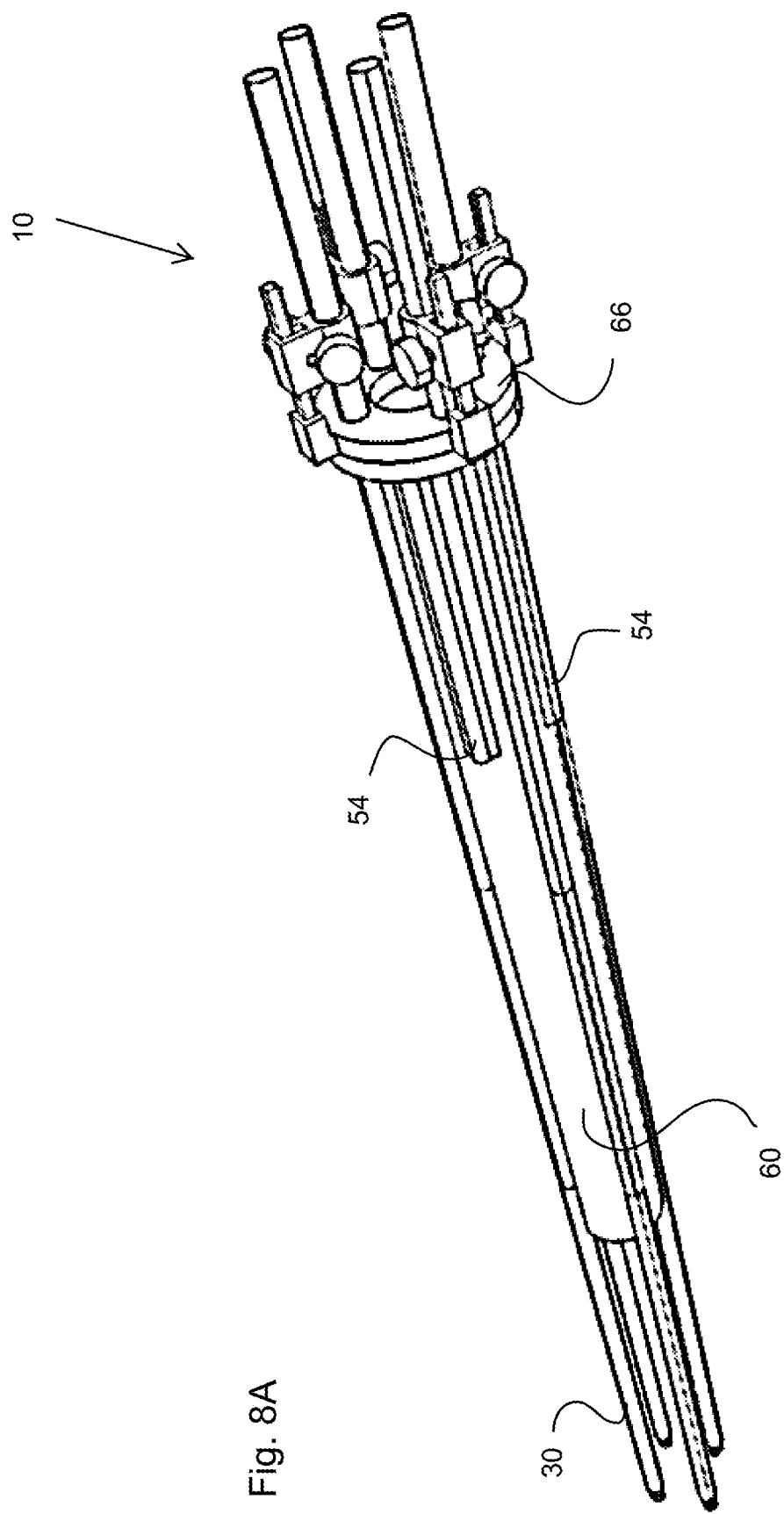
FIG. 8A is rear bottom side perspective view of the cylindrical insert of cylindrical insert of FIG. 7A, stabilizing four K wires, with the optional clamp at a posterior end of the cylindrical insert.
Figure 10:
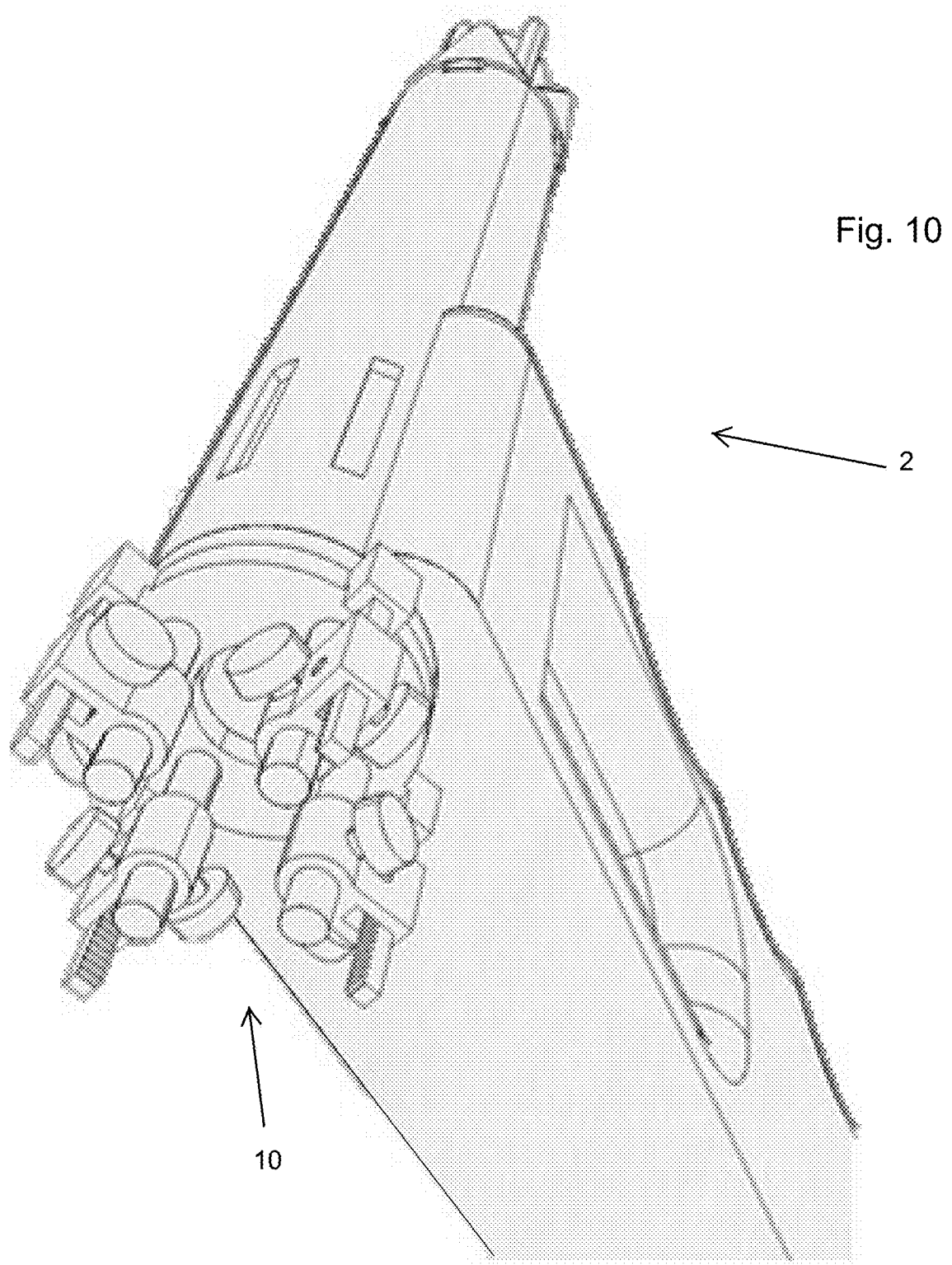
FIG. 10 is a rear bottom side perspective view of tissue protector of FIG. 1B, with the insert, pins, and clamp of FIG. 8A.

When the soft tissue protector 2 is in contact with the patient bone and it is anchored using pins 30, for example with self-tapping, a clamp 10 may be anchored to the tool. The clamp 10 allows the controlled displacement of each single pin 30 as shown in FIGS. 8A, 8B and 10. The clamp 10 can be used to fine tune the orientation of the soft tissue protector in relation to the bone. The mechanism for the fine positioning clamp 10 allows the independently advancing or retracting the relative position of the pins 30. The clamp 10 may be rigidly connected to the insert 6 at a clamp base 66, and connects individually to the surgical pins via a plurality of rack and pinon units 68. The rack and pinon units 68 include a toothed 70 rack 72 that supports a pinon box 74. A height adjuster 76 moves the pinon box up and down the rack 72, and a tension adjuster 78 increases or decreases the diameter of a pinon box extension of the pocket 62, thereby releasing or retaining the pin axially stationary with relation to the pinon box 74.

As shown in FIG. 9, the intraoperative tracking of the tool can be performed using x-ray with radiopaque tip inserts 80 on the anterior end 16 of the hollow body 4, and/or with ring inserts 82 placed around the hollow body 4.

In addition, inertial or optical markers 84 can be attached posteriorly as shown in FIG. 11, and be used to track the soft tissue protector's 2 position in real time surgical navigation.

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

Wherefore, we claim:

1. A soft tissue protector comprising: a hollow body; a plurality of jaws at an anterior end of the hollow body forming a conical tip; and an insert that is inserted inside of a posterior end of the hollow body, wherein a post hole is defined along an inner surface of each of the jaws, and a corresponding post is placed at an anterior end of the insert, each post being aligned with a respective post hole and locking each respective jaw in a closed position.

2. The soft tissue protector of claim 1 further comprising at least one handle.

3. The soft tissue protector of claim 2, further comprising a sliding lock on the handle that retains the insert inside of the hollow body.

4. The soft tissue protector of claim 1 further comprising two handles, mounted on opposite radial sides of the hollow body.

5. The soft tissue protector of claim 1 wherein the insert has one or more radial tabs extending axially along a radially exterior surface, the radial tabs aligning with tab grooves axially extending along a radially inner surface of an interior of the hollow body.

6. The soft tissue protector of claim 1 wherein the plurality of jaws is spring biased in a closed position.

7. The soft tissue protector of claim 1 wherein an anterior end of the plurality of jaws define a central hole that allows passage to one of a surgical pin or a Kirschner wire.

8. The soft tissue protection of claim 1 wherein a central pathway is defined by an inner radial surface of the insert, allowing the passage of surgical tools within.

9. The soft tissue protector of claim 1 further comprising a radiopaque insert on the hollow body.

10. The soft tissue protector of claim 9, wherein the radiopaque insert is a radiopaque tip insert and is disposed on anterior end of one or more jaws.

11. The soft tissue protector of claim 9, wherein the radiopaque insert is a radiopaque ring insert and is disposed around an outer circumference of the hollow body, adjacent to the anterior end of the hollow body.

12. The soft tissue protector of claim 1 further comprising a navigation marker attached to a posterior end of the hollow body.

13. The soft tissue protector of claim 12, wherein the navigation marker is an inertial marker.

14. The soft tissue protector of claim 1 further comprising an optical marker.

15. A soft tissue protector comprising: a hollow body; a plurality of jaws at an anterior end of the hollow body forming a conical tip; and an insert that is inserted inside of a posterior end of the hollow body, wherein one or more pockets are present in a radially exterior surface of the insert and a radially interior surface of the hollow body, the pockets sized to support and allow passage of one of a surgical pin or a Kirschner wire.

16. The soft tissue protector of claim 15 further comprising a clamp, which axially secures the one of a surgical pin or a Kirschner wire in a stationary axial position relative to the soft tissue protector.

17. The soft tissue protector of claim 16, wherein the clamp includes a rack and pinon.

18. The soft tissue protector of claim 17, wherein there are four pocket and a rack and pinon unit for each pocket.

19. A soft tissue protector comprising:
a hollow body;
a plurality of jaws at an anterior end of the hollow body forming a conical tip, the plurality of jaws is spring biased in a closed position;
an insert that is inserted inside of a posterior end of the hollow body;
at least one handle;
a sliding lock on the handle that retains the insert inside of the hollow body;
tab grooves axially extending along a radially inner surface of an interior of the hollow body;
a plurality of radial tabs extending axially along a radially exterior surface of the insert, the radial tabs aligning with tab grooves;
a central hole defined in an anterior end of the plurality of jaws, the central hole allowing passage of one of a surgical pin or a Kirschner wire;
a post hole being defined along an inner surface of each of the jaws;
a post is placed at an anterior end of the insert, each post being aligned with a respective post hole and locking each respective jaw in a closed position when the insert is sufficiently inserted into the hollow body;
a central pathway is defined by an inner radial surface of the insert, allowing the passage of surgical tools within;
four pockets are present in a radially exterior surface of the insert and a radially interior surface of the hollow body, the pockets sized to support and allow passage of one of a surgical pin or a Kirschner wire;
a clamp, which axially secures the one of a surgical pin or a Kirschner wire in a stationary axial position relative to the soft tissue protector; the clamp including a rack and pinon unit for each pocket; and
one of
a radiopaque tip insert disposed on anterior end of one or more jaws,
a radiopaque ring insert disposed around an outer circumference of the hollow body, adjacent to the anterior end of the hollow body,
an optical navigation marker attached to a posterior end of the hollow body, and an inertial navigation marker attached to a posterior end of the hollow body.

\* \* \* \* \*